United States Patent [19]
Ho

[11] Patent Number: 5,964,797
[45] Date of Patent: Oct. 12, 1999

[54] ELECTROLYTICALLY DEPLOYABLE BRAIDED VASO-OCCLUSION DEVICE

[75] Inventor: Liem Ho, Mountain View, Calif.

[73] Assignee: Target Therapeutics, Inc., Fremont, Calif.

[21] Appl. No.: 08/706,075

[22] Filed: Aug. 30, 1996

[51] Int. Cl.⁶ .................................. A61F 2/06; A61F 2/02
[52] U.S. Cl. ........................................ 623/1; 623/11
[58] Field of Search ........................ 623/1, 12, 24, 623/25; 606/32, 41, 108, 213, 157, 158, 194

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 4,739,768 | 4/1988 | Engelson . |
| 4,884,575 | 12/1989 | Sanders . |
| 4,994,069 | 2/1991 | Ritchart et al. . |
| 5,067,491 | 11/1991 | Taylor, II et al. . |
| 5,122,136 | 6/1992 | Guglielmi et al. . |
| 5,174,295 | 12/1992 | Christian et al. . |
| 5,250,071 | 10/1993 | Palermo . |
| 5,304,194 | 4/1994 | Chee et al. ................................. 623/11 |
| 5,354,295 | 10/1994 | Guglielmi et al. . |
| 5,380,320 | 1/1995 | Morris et al. . |
| 5,382,259 | 1/1995 | Phelps et al. ................................. 623/1 |
| 5,423,829 | 6/1995 | Pham et al. . |
| 5,522,822 | 6/1996 | Phelps et al. ........................... 606/151 |
| 5,522,836 | 6/1996 | Palermo ........................................ 623/1 |
| 5,582,619 | 12/1996 | Ken ............................................. 623/1 |
| 5,624,449 | 4/1997 | Pahm et al. .............................. 606/108 |

FOREIGN PATENT DOCUMENTS

| | | |
|---|---|---|
| WO 94/10936 | 5/1994 | WIPO . |
| WO 94/15534 | 7/1994 | WIPO . |
| WO 94/16632 | 8/1994 | WIPO . |

Primary Examiner—John G. Weiss
Assistant Examiner—John M. Black
Attorney, Agent, or Firm—Morrison & Foerster LLP

[57] ABSTRACT

This is a braided tubular device used in the occlusion of various lumen or cavities in the body. In particular, it may be used to form an endovascular occlusion. Most desirably, it is braided of a majority of super-elastic alloy ribbons and therefore is both inherently non-stretching and most difficult to permanently deform. It may be deployed using an electrolytically severable joint. A radio-frequency modulated current may optionally be applied to the device after its placement in the body. The elongated device preferably is insulated along its length to optimize its occlusive activity without harm to the body.

9 Claims, 2 Drawing Sheets

ELECTROLYTICALLY DEPLOYABLE BRAIDED VASO-OCCLUSION DEVICE

FIELD OF THE INVENTION

This invention is a braided tubular device used in the occlusion of various lumen or cavities in the body. In particular, it may be used to form an endovascular occlusion. Most desirably, it is braided of a majority of super-elastic alloy ribbons and therefore is both inherently non-stretching and most difficult to permanently deform. It may be deployed using an electrolytically severable joint. A radio-frequency modulated current may optionally be applied to the device after its placement in the body. The elongated device is insulated along its length to optimize its occlusive activity without harm to the body.

BACKGROUND OF THE INVENTION

A wide variety of medical procedures are facilitated by occluding such body lumens and cavities as the arteries, veins, vascular aneurysms, various vascular malformations (e.g., AVM's), fallopian tubes, vas deferens, ureters, and the like. For instance, an extravascular approach to treatment of aneurysms involves surgically exposing or stereotaxically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by reference.

A still further approach is the least invasive and is additionally described in Guglielmi et al. It is the endovascular approach. In this approach, the interior of the aneurysm is entered by use of a catheter such as those shown in Engelson (Catheter Guidewire), U.S. Pat. No. 4,884,575 and also in Engelson (Catheter for Guidewire Tracking), U.S. Pat. No. 4,739,768. These procedures utilize endovascular guidewires and catheters, introduced quite remotely, to access the aneurysm. Specifically by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of the difficulty in introducing the balloon into the aneurysm sac, the possibility of an aneurysm rupture due to overinflation of the balloon within the aneurysm, and the risk associated with the traction produced when detaching the balloon.

A highly desirable occlusive device which may be introduced to a selected body site using endovascular placement procedures, is found in U.S. Pat. No. 4,994,069, to Ritchart et al. There is described a device—typically a platinum/tungsten alloy coil having a very small diameter—which may be introduced to the selected site through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as found in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136) as was discussed above.

Guglielmi et al. shows an embolism-forming device and procedure for using that device. Specifically, Guglielmi et al. fills a vascular cavity such as an aneurysm with an embolic device such as a platinum coil which coil has been endovascularly delivered. The coil is then severed from its insertion tool by the application of a small electric current. Desirably, the insertion device involves a guidewire which is attached at its distal end to an embolic device by an electrolytic, sacrificial joint. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety of ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

A further variation of the Guglielmi detachable coil is one in which the distal tip of the stainless steel guidewire is not soldered to the proximal end of the embolic device. A simple conical stainless steel wire is included from the stainless steel guidewire to the embolic coil.

A further variation found in Guglielmi et al. includes a thin, threadlike extension between the guidewire core and the proximal end of the embolic coil. In this way, the guidewire does not extend to the embolic coil, but instead relies upon a separately introduced extension.

A continuation-in-part application to the Guglielmi et al patent discussed above, U.S. Pat. No. 5,354,295, "IMPROVEMENTS IN AN ENDOVASCULAR ELECTROLYTICALLY DETACHABLE WIRE AND TIP FOR THE FORMATION OF THROMBUS IN ARTERIES, VEINS, ANEURYSMS, VASCULAR MALFORMATIONS AND ARTERIOVENOUS FISTULAS" issued Oct. 11, 1994, describes the use of mechanically detachable embolic devices as well as those which are electrolytically detachable. The embolic devices may be augmented with attached filaments.

Dr. Taki has devised a variation of the Guglielmi detachable coil using a copper link between the guidewire and the coil.

None of these devices utilize an electrolytically detachable braid element which comprises a majority of super-elastic alloy ribbons, a radio-opaque marker element, and an outer insulative layer.

SUMMARY OF THE INVENTION

As noted above, this invention is a device used in forming an occlusion at a selected site typically within the human body. In general, the device comprises a braided elongated body having a proximal end and a distal end. The braided elongate tubular body is made using a majority of super-elastic alloy ribbons and some type of a radio-opaque marker. The body length between those ends has a longitudinal axis and typically a lumen running within the elongated body. The elongated body is typically tubular although it need not be. An electrolytically detachable joint is often found at the proximal end of the elongated body member. Central to this invention is the presence of an insulating layer over the exterior of the body member. The proximal portion and the connective joint are electrically conductive. Because of the use of the braided structure and the super-elastic alloy, the device retains its shape and does not deform to any appreciable extent during a deployment procedure.

The inventive device is typically used in conjunction with a DC source for dissolution of the joint and may also be used with an AC source, or a modulated RF source in such a way that it either produces an occlusion in the chosen body site or constricts the lumen into which it is placed. In the latter instance, the device is often left at the selected site but in some occasions may be removed if such is desired by the attending physician.

DESCRIPTION OF THE INVENTION

Figure 1:
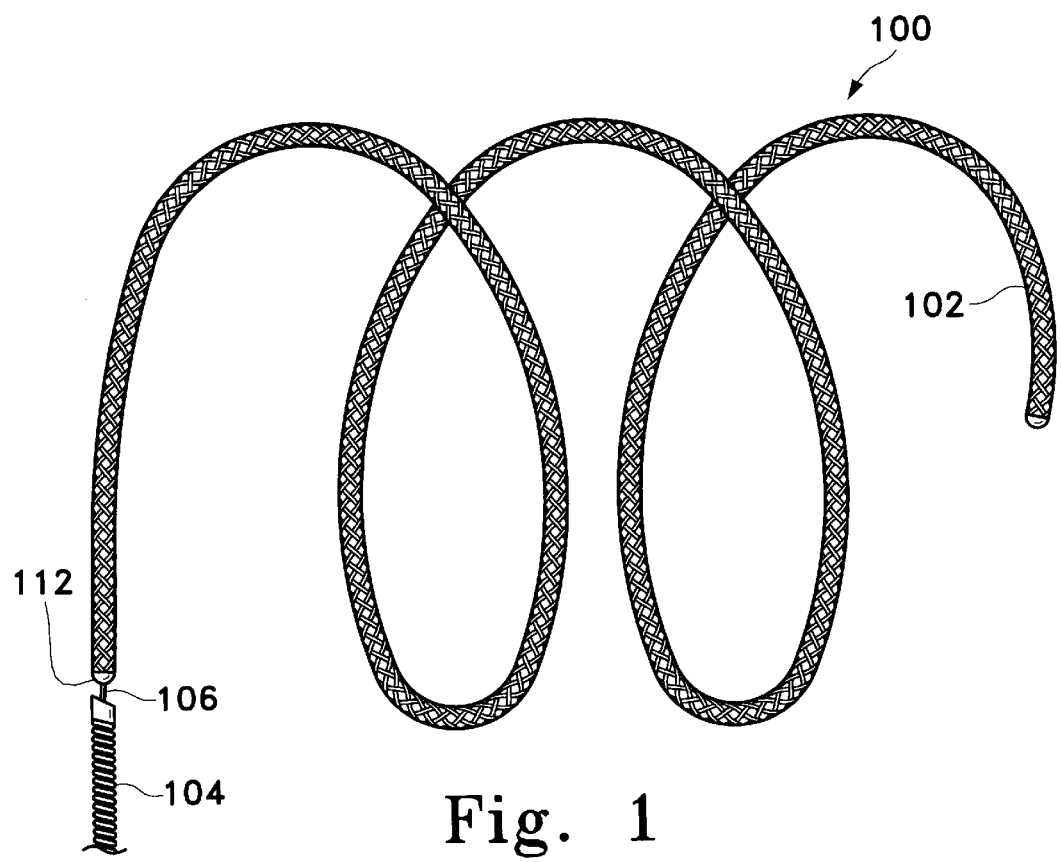
FIG. 1 shows a side view of a typical device made according to this invention.

FIG. 1 provides a side view of a generic representation of the inventive device (100). In this view, three important portions of the device may be seen: the braided occlusive device (102), the pusher element (104) and the connective joint (106).

As has been discussed above, this invention may be used in conjunction with the procedure discussed in the Guglielmi patents. In the earlier described Guglielmi procedures, a DC current is sent through an insulated wire or pusher connected to the vaso-occlusive device. The current is held at a level sufficient to cause a specially designed joint located just proximal of the vaso-occlusive coil itself to erode thereby allowing the connective wire to be withdrawn. Once the connective wire is withdrawn, the coil forms an embolus at the desired site in the vasculature. Such a site might be, for instance, within an aneurysm. This invention may be used in that variation of the Guglielmi procedure.

Optional to this invention is the radio-frequency variation of the Guglielmi procedure, which procedure is described in U.S. patent application Ser. No. 08/499,525 (Attorney Docket 290252013200), the entirety of which is incorporated by reference. In essence, the latter variation desirably involves the imposition of a radio-frequency signal into the device for the specific purpose of causing a spasm in the blood vessel (or other lumen or cavity) and thereby causing a collapse of the vessel wall onto the coil. It is this formation of a region of collapse that distinguishes the later Guglielmi procedure from the earlier method.

The invention described herein may be used in either procedure. We have observed that when using the radio-frequency version of the method, that if at least the distal end of the device is left unprotected (that is to say "uninsulated") then the distal end has a tendency to erode or even to perforate the vessel wall.

The braided section (102) comprises a braided tubular structure made up of a plurality of interwoven ribbon or fibrous members, a majority of which comprise one or more super-elastic and (preferably) ternary alloys of nickel, titanium, and optionally at least about 1.5% (wt) of one or more alloying members selected from the group consisting of vanadium, chromium, manganese, iron, and cobalt. The braided structure may contain a minority of fibrous members of radio-opaque materials, polymeric materials, other metals or alloys, and highly conductive materials. Highly conductive materials are considered to be those having a specific resistance less than about 100 ohms per foot, preferably less than 50 ohms per foot, and most preferably less than about 10 ohms per foot. Once the braid is woven, it preferably is heat treated to "set" the woven structure in its tubular form. The braid structure of this invention is particularly desirable because of its consistency of size (e.g., diameter) and physical properties (e.g., flexibility). Because of the suppleness of the smaller sizes of the component braid, it is especially useful as a vaso-occlusive device since it does not cause substantial damage to the intima. Yet the material and structure provide significant ability to maintain a desired position in the selected vascular site through the gentle pressure against the vascular wall. The device may be used as electromagnetic shielding during various diagnostic procedures.

Figure 2:
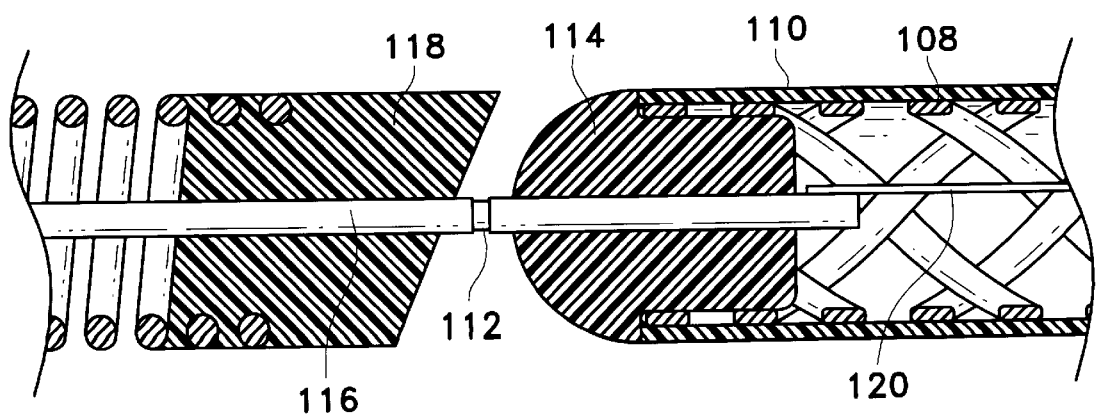
FIG. 2 shows a side view partial cutaway of the electrolytic joint made according to the invention.

FIG. 2 shows one variation of the metallic braid (102) made up of a number of metallic ribbons (108). A majority of the metallic ribbons (108) in braid (102) are super-elastic alloys. In this variation, there is a significant amount of spacing between adjacent turns of the braid ribbons.

A technical basis for super-elastic alloys is found in the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. Alloys especially suitable for use in the inventive device are those which also contain at least 1.5% (wt) and up to about 8% (wt) or more, of one or more alloying members selected from the group consisting of vanadium, chromium, manganese, iron, and cobalt.

When using such super-elastic alloys, an additional step may be desirable to preserve the shape of the braid. For instance, with a Cr-containing Ni/Ti super-elastic alloy which has been rolled into a 1×4 mil ribbon and formed into a 16-member braid, some heat treatment is desirable. The braid may be placed onto a mandrel, usually metallic, of an appropriate size. The braid is then heated to a temperature of 650°–750° F. for a few minutes, possibly (but not necessarily) annealing the constituent ribbon. After heat treatment, the braid retains its shape and the alloy retains its super-elastic properties.

In the event that a coil-like shape such as is shown in FIG. 1 is desired, the mandrel may have the coil-like shape shown there as well. Alternatively, the braid with (or without) its heat treatment mandrel may be woven onto a second mandrel for a secondary heat treatment step to provide the coil-like shape shown in the FIG. 1. Other shapes are obviously desirable as well.

Metallic ribbons (108) that are suitable for use in this invention are desirably between 0.25 mil and 3.5 mil in thickness and 2.5 mil and 12.0 mil in width. The term "ribbon" is intended to include elongated shapes, the cross-section of which are not square or round and may typically be rectangular, oval or semi-oval. They should have an aspect ratio of at least 0.5 (thickness/width).

The braid shown in the Figures may contain a minor number of ribbons (108) which are non-super-elastic materials. Although metallic ribbons may be preferred as the ancillary materials because of their strength-to-weight ratios, fibrous materials (both synthetic and natural) may also be used. Preferred, because of their radio-opacity, are radio-opaque metals and alloys, e.g., gold, platinum, palladium, rhodium, rhenium, tungsten, their alloys and mixtures, etc. A platinum alloy with a few percent of tungsten is preferred partially because of its radio-opacity. In certain applications, where cost, strength, and ready availability are criteria, stainless steels (SS304, SS306, SS308, SS316, SS318, etc.) and tungsten alloys may comprise the ribbons.

Suitable non-metallic ribbons include high performance materials such as those made of polyaramids (e.g., KEVLAR) and carbon fibers.

The braids of this invention may be made using commercially available tubular braiders. The term "braid" is meant to include tubular constructions in which the fibrous materials making up the construction are woven in an in-and-out fashion as they cross to form a tubular member defining a single passageway. The braids may be made up of a suitable number of ribbons, typically six or more. Ease of production on a commercial braider typically results in braids having eight or sixteen ribbons.

The braided structures shown in FIGS. 1 and 2 have a nominal pitch angle of 45°. Clearly the invention is not so limited. Other braid angles from 20° to 60° are also suitable. An important variation of this invention is the ability to vary controllably the pitch angle of the braid either at the time the braid is woven or at the time the braid is assembled into another device.

Although the braid (102) shown the in Figures has a single size of ribbon, the braid need not be so limited; multiple sizes of ribbon may be used as desired. The major limitations are simply the size, e.g., diameter, of the overall braid as finally constructed and the desired added stiffness to be added to the braid structure.

The braids typically useful in this invention comprise an even number of ribbons: one half of the ribbons wound one way, i.e., clockwise, and the remainder are wound the other way. A typical braid will be of four to 16 ribbons. The braid may have a single pitch, an angle of a constituent ribbon measured against the axis of the braid, or it may have a pitch which varies along the axis of the braid.

The braid structure (102) shown in FIG. 1 has a relatively constant diameter. Although the heat treatment step noted above in conjunction with the specified alloys results in a tubular structure having a shape corresponding to the particular mandrel chosen for the heat treating step, the shape of the mandrel and hence the shape of the tubular structure may have a varying, e.g., an increasing or decreasing diameter.

The braid structure (102) may be rough to the touch if not covered or further processed. Procedures such as rolling, sanding, or grinding may be used to smooth the surface of the braid structure if so desired. Removal of any produced particulates is, of course, desirable.

The spacing between the adjacent ribbons (108) may be minimal. That is to say that each ribbon (108) is adjacent the next. This tight structure is typically stiffer than more loosely woven braids.

Another variation of the depicted braid is a structure in which the filamentary members are not a single weave as is shown in the Figures above. Instead, the filamentary members weave around the tubular structure in a band of (for instance) four to five filaments much in the same way that the single ribbon is woven around the FIG. 1 and 2 devices. This variation is nominated a "multiple member braid structure."

The axial length of the device as deployed will usually fall in the range of 0.10 to 100 cm. If used with a radio-frequency version the length is typically 0.25 to 0.75 cm., more preferably about 0.5 cm. If used in other procedures, the length is more usually 2.0 to 40 cm. Depending upon usage, the braid may well have 10–75 pics per centimeter, preferably 10–40 pics per centimeter. For most neurovascular indications, the preferable device diameter is 0.006 to 0.018 inches. Each of the dimensions is provided only as a guideline and is not critical to the invention. However, only dimensions suitable for use in occluding sites within the human body are included in the scope of this invention.

FIG. 2 shows an exterior covering (110) of an insulative polymer placed directly upon the braid ribbons (108). In general, by "insulative" is meant that the insulator has a resistance of 500 kilohms/cm or greater. The insulation typically is a polymer such as polyethylene, polypropylene, polyurethane, polyethylene terephthalate, polyvinylchloride, polytetrafluoroethylene or the like and may be applied by a number of procedures, depending in large part on the composition of the polymer. They may be applied by shrink-wrapping the insulators onto the device in the form of tubing. The device may be dipped in molten polymer. The insulation may be sprayed on in the form of a suspension or latex. Each of these procedures and polymers has benefits and detriments, e.g., added stiffness or complicated adjuvant process steps.

One very desirable thermoplastic insulator is generically known as parylene. There are a variety of polymers (e.g., polyxyxylene) based on paraxylylene. These polymers are typically placed onto a substrate by vapor phase polymerization of the monomer. Parylene N coatings are produced by vaporization of a di(P-xylylene) dimer, pyrolization, and condensation of the vapor to produce a polymer that is maintained at a comparatively lower temperature. In addition to parylene-N, parylene-C is derived from di(monochloro-P-xylylene) and parylene-D is derived from di(dichloro-P-xylylene). There are a variety of known ways to apply parylene to substrates. Their use in surgical devices has been shown, for instance, in U.S. Pat. No. 5,380,320 (to J. R. Morris), in U.S. Pat. No. 5,174,295 (to Christian et al.), in U.S. Pat. No. 5,067,491 (to Taylor et al.) and the like. A coating of less than about 0.001" is highly desirable, preferably less than about 0.00075", e.g., about 0.0002". A parylene coating has the benefits of being very thin and very flexible. Because it may be applied in a vapor-phase process, the masking of the electrolytically erodible region (112) is easily accomplished during coating of the insulated regions.

FIG. 2 also shows a plug or tip (114) which may also be a polymeric material such as various thermoplastics or epoxides and a pusher facing (118) which is also formed of an insulative material.

FIG. 2 also shows the essential details of the electrolytic joint (112). The detachable embolic braided device (102) is insulated from the surrounding blood (or other ionic fluid) and consequently when a current is applied to the core wire (116), the current flows into the surrounding ionic medium through the electrolytic joint (112) back to the power source (not shown) while dissolving the joint (112). The areas just adjacent the electrolytic joint (112) are insulated, perhaps much in the same way and with the same material that the braid structure is covered. The length of the exposed electrolytic dissolution area (112) is quite short. For instance, it may be as short as 0.010 inches, and typically is no longer than 0.150 inches in length.

As noted above, it is useful to add a measure of radio-opacity to the braided vaso-occlusive device. An alternative to using radio-opaque materials as braid ribbons is shown in FIG. 2. A radio-opaque member (120) is included in the lumen within the braid member and passes from one end of the braid member to the other. The radio-opaque member (120) may be a ribbon or wire or the like and is preferably joined to the core wire (116) as shown.

Additional details on the construction of effective electrolytic joints may be found in U.S. Pat. No. 5,423,829, to Pham et al, and in U.S. Ser. No. 08/367,061 and its continuation Ser. No. 08/485,502, to Gia et al, the entirety of which are incorporated by reference.

Placement of the device (100) in the body may be achieved by the methods described in a variety of patents, e.g., U.S. Pat. No. 4,994,069, to Ritchart et al. In this approach, a chosen vascular site, such as an aneurysm, is entered by use of a catheter such as those shown in Engelson (Catheter Guidewire), U.S. Pat. No. 4,884,575 and also in Engelson (Catheter for Guidewire Tracking), U.S. Pat. No. 4,739,768. These patents describe procedures using guidewires and catheters which allow access to the site from remote portions of the body. Specifically, by the use of catheters having very flexible distal regions and guidewires which are steerable to the region of the aneurysm, embolic devices may be delivered through the catheter to the remote vascular site. The guidewires described in these patents typically have a soft distal tip which may be bent or "formed" by the physician using the device to allow the guidewire to be used to select a path at a junction between vessels.

Figure 3:
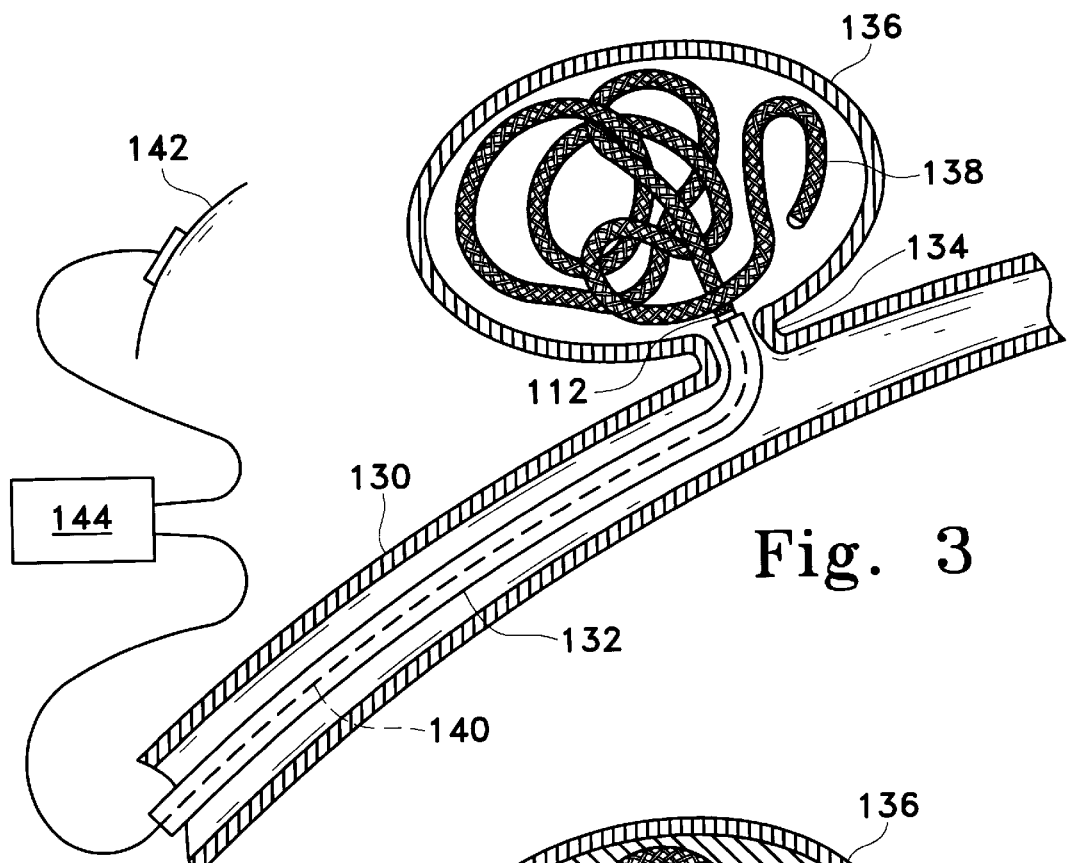
FIGS. 3 and 4 schematically depict the method for deploying the vaso-occlusive device.

FIG. 3 shows the placement of the inventive devices shown above within a vessel (130) with the tip of catheter (132) placed near neck (134) of aneurysm (136). Braided vaso-occlusive device (138) is fed into aneurysm (136) at least until sacrificial link (112) is exposed beyond the distal tip of the catheter (132). A positive electric current of approximately 0.01–2 milli-amps at 0.1–6 volts is applied to core wire (140) to form a thrombus (141) within aneurysm (136). The negative pole (142) of power supply (144) is typically placed in electrical contact with the skin. It is also desirable that the current be allowed to return through a conductor placed in the wall of the catheter (or the guide catheter used in conjunction with the catheter).

As the thrombus (141) is formed and the aneurysm (136) occluded, vaso-occlusive device (138) is detached from core wire (140) by electrolytic disintegration of sacrificial link (112).

Figure 4:
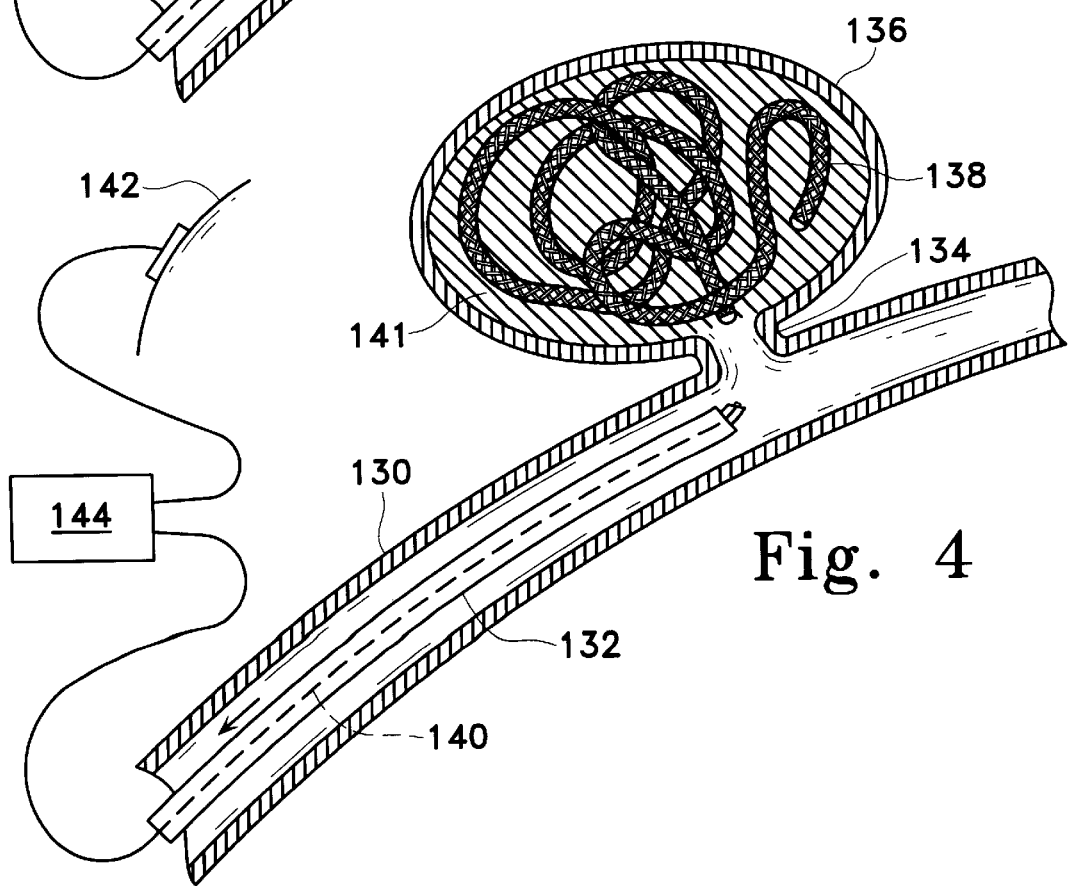

After sacrificial link (112) is completely dissolved by electrolytic action, typically within 5 seconds to 5 minutes, the core wire (140) and catheter (132), are removed from the vessel (130), leaving aneurysm (136) occluded as shown in FIG. 4.

The process is typically practiced under fluoroscopic control with local anesthesia. A transfemoral catheter is utilized to treat a cerebral aneurysm and is usually introduced at the groin. When the core wire and pertinent portions of the supporting coils at the distal tip of the guidewire are adequately coated with insulating coverings, only the exposed portion at the sacrificial link (112) is affected by the electrolysis.

Procedures for using this invention in non-vascular systems of the body are carried out in a similar fashion. The chosen site must be accessible and the site must provide a local medium of sufficient ionic nature to allow electrolysis of the sacrificial joint to take place.

The illustrated embodiments have been used only for the purposes of clarity and should not be taken as limiting the invention as defined by the following claims.

I claim as my invention:

1. An occluding device for placement in the human body comprising an elongated body member formed from a plurality of ribbons, said ribbons being braided with each other, at least a majority of said ribbons are formed from super-elastic alloys, said body member having a proximal end and a distal end and a lumen between said proximal and distal ends, an electrolytically detachable joint attached to said proximal end capable of conducting an electrical current through said joint to said body member, and wherein said body member is substantially covered with a polymeric insulative material.

2. The device of claim 1 wherein a minority of said ribbons comprise a radio-opaque material selected from the group consisting of gold, platinum, palladium, rhodium, rhenium, tungsten, their alloys and mixtures.

3. The device of claim 2 wherein a minority of said ribbons comprise a platinum alloy with tungsten.

4. The device of claim 1 further comprising a radio-opaque member traversing at least a portion of the lumen.

5. The device of claim 4 wherein said radio-opaque member comprises a radio-opaque material selected from the group consisting of gold, platinum, palladium, rhodium, rhenium, tungsten, their alloys and mixtures.

6. The device of claim 5 wherein said radio-opaque member comprises a platinum alloy with tungsten.

7. The device of claim 1 wherein said polymeric insulative material comprises a member selected from the group consisting of polyethylene, polypropylene, polyurethane, polyethylene terephthalate, polyvinylchloride, polytetrafluoroethylene, and polyxyxylene.

8. The device of claim 1 wherein said polymeric insulative material comprises polyxyxylene.

9. The device of claim 1 wherein said polymeric insulative material comprises polytetrafluoroethylene.

* * * * *